(12) United States Patent
Varahramyan et al.

(10) Patent No.: US 9,044,158 B2
(45) Date of Patent: Jun. 2, 2015

(54) WEARABLE MICROSTRIP ANTENNAS FOR SKIN PLACEMENT FOR BIOMEDICAL APPLICATIONS

(75) Inventors: Khodadad Varahramyan, Indianapolis, IN (US); Mangilal Agarwal, Indianapolis, IN (US); Sudhir Shrestha, Indianapolis, IN (US)

(73) Assignee: Indiana University Research and Technology Corp., Indianapolis, IN (US)

( * ) Notice: Subject to any disclaimer, the term of this patent is extended or adjusted under 35 U.S.C. 154(b) by 527 days.

(21) Appl. No.: 13/077,387

(22) Filed: Mar. 31, 2011

(65) Prior Publication Data

US 2011/0245653 A1    Oct. 6, 2011

Related U.S. Application Data

(60) Provisional application No. 61/319,715, filed on Mar. 31, 2010.

(51) Int. Cl.
| | |
|---|---|
| *H01Q 1/38* | (2006.01) |
| *A61B 5/05* | (2006.01) |
| *H01Q 1/24* | (2006.01) |
| *H01Q 9/16* | (2006.01) |
| *A61B 5/00* | (2006.01) |

(52) U.S. Cl.
CPC .. *A61B 5/05* (2013.01); *H01Q 1/38* (2013.01); *H01Q 1/243* (2013.01); *H01Q 9/16* (2013.01); *A61B 5/0507* (2013.01); *A61B 5/441* (2013.01)

(58) Field of Classification Search
CPC ............ H01Q 9/16; H01Q 1/38; H01Q 1/243
USPC .................................................. 343/700 MS
See application file for complete search history.

(56) References Cited

U.S. PATENT DOCUMENTS

| | | | |
|---|---|---|---|
| 5,829,437 A | 11/1998 | Bridges | |
| 6,061,589 A | 5/2000 | Bridges et al. | |
| 7,266,407 B2 | 9/2007 | Li et al. | |
| 7,340,292 B2 | 3/2008 | Li | |
| 7,454,242 B2 | 11/2008 | Fear et al. | |
| 7,647,089 B2 | 1/2010 | Bond et al. | |
| 2004/0077943 A1 | 4/2004 | Meaney et al. | |
| 2004/0167399 A1* | 8/2004 | Li | ................................. 600/430 |
| 2005/0052322 A1* | 3/2005 | Park et al. | .............. 343/700 MS |
| 2010/0067770 A1 | 3/2010 | Persson et al. | |

OTHER PUBLICATIONS

Sandu, D.; "Microstrip Patch Antenna With Dielectric Substrate"; Journal of Optoelectronics and Advanced Materials, vol. 5, No. 5, 2003 (7 pages).

* cited by examiner

*Primary Examiner* — Graham Smith
(74) *Attorney, Agent, or Firm* — Maginot Moore & Beck LLP

(57) ABSTRACT

A method of imaging biological tissue enables imaging structure in the biological tissue with an antenna tuned to emit radio energy through at least a covering layer of the biological tissue without significant attenuation of the radio energy. The method includes contacting skin covering tissue with a radio frequency emitting antenna, and adjusting at least one of a radiator and a feed in the antenna with reference to at least one measured electrical or physical property of the skin. The adjustment of the radiator and feed enable a combination of the antenna and skin to emit radio energy at a predetermined magnitude and frequency into a portion of the tissue covered by the skin.

5 Claims, 10 Drawing Sheets

US 9,044,158 B2

WEARABLE MICROSTRIP ANTENNAS FOR SKIN PLACEMENT FOR BIOMEDICAL APPLICATIONS

PRIORITY CLAIM

This application claims priority from U.S. Provisional Application No. 61/319,715, which is entitled "WEARABLE MICROSTRIP ANTENNAS FOR SKIN PLACEMENT FOR BIOMEDICAL APPLICATIONS" and was filed on Mar. 31, 2010.

TECHNICAL FIELD

The system and method described below relate to the detection and imaging of subdermal structures and growths in a living organism, in particular a human being.

BACKGROUND

The field of medical imaging includes many well-known techniques for subdermal imaging of tissues and structures beneath the skin of a patient in a non-invasive manner. These imaging techniques commonly emit a form of electromagnetic energy that penetrates one or more tissue layers of the patient. Common examples of existing medical imaging techniques include X-Rays, positron emission tomography (PET) scans, and ultrasounds. A more recently developed medical imaging technique transmits microwave energy into a patient's body. This technique detects structures within the patient's body by detecting the reflections or backscatter occurring when the microwaves encounter a structure that reflects the microwave energy.

Subdermal imaging has many possible medical applications, and one application of immediate importance is the detection of growths and tumors in breast tissue. Breast cancer is a serious disease that kills tens of thousands of women every year in the United States alone. The use of X-Ray mammography has helped to detect breast tumors earlier, allowing early treatment that greatly improves the survival rate. However, X-Rays are high-energy ionizing radiation known to promote the development of cancers in human tissue. Thus, there is an undesirable tradeoff between not testing breast tissue for cancer and risking an undetected cancerous growth, or testing more often and increasing the risk that the testing technique itself will cause cancer to develop. Other imaging techniques that avoid the use of ionizing radiation such as an ultrasound may be much less effective at detecting tumors in the breast tissue.

Microwave imaging techniques present many advantages over other imaging techniques for detecting cancerous tumors, especially tumors in breast tissue. Unlike the energy used in an X-Ray, microwave energy is non-ionizing when penetrating human tissue. The non-ionizing radiation does not pose the cancer risk of the ionizing X-Ray radiation. Further, tumors in breast tissue are known to have a significant and consistent contrast to the microwaves in comparison to surrounding healthy breast tissue. The significant contrast characteristic means that a microwave that passes through healthy breast tissue also reflects off the surface of a tumor. By detecting the backscatter pattern of the reflected microwave energy, the tumor can be detected and imaged non-invasively.

While microwave imaging techniques have many advantages, the structure of the human body presents difficulties in using microwave imaging devices to effectively identify and image tumors. One such problem is that the human body has many layers of heterogeneous tissues, with the skin being the outermost layer. As stated above, microwave energy passes through the healthy breast tissue and reflects off the surface of cancerous growths. However, the microwaves also tend to reflect off the surface of human skin, which is often referred to as the "skin reflection." The skin reflection causes noise in the reflected microwave signals, potentially obscuring reflections that may come from a tumor inside the patient's body from reflections are merely from the patient's skin. A system for microwave imaging that reduces noise introduced by the skin reflection benefits the fields of biomedical imaging and oncology.

SUMMARY

A method of imaging biological tissue enables imaging structure in the biological tissue with an antenna tuned to emit radio energy through at least a covering layer of the biological tissue without significant attenuation of the radio energy. The method includes contacting skin covering tissue with a radio frequency emitting antenna, and adjusting at least one of a radiator and a feed in the antenna with reference to at least one measured electrical or physical property of the skin. The adjustment of the radiator and feed enabling a combination of the antenna and skin to emit radio energy at a predetermined magnitude and frequency into a portion of the tissue covered by the skin.

A system for imaging biological tissue has been developed. The system includes a radio signal generator, a radio signal receiver, at least one antenna electrically connected to the radio signal generator and radio signal receiver, and an imaging device communicatively coupled to the radio signal receiver. The at least one antenna is configured to couple with skin tissue to enable an antenna/skin tissue combination to radiate energy at a predetermined magnitude and frequency into at least one other layer of biological tissue covered by the skin tissue. The imaging device is configured to generate a two-dimensional or three-dimensional display of the biological tissue based on backscatter energy received from the biological tissue by the radio signal receiver.

An antenna system has been developed for the biological tissue imaging system. The antenna system includes a plurality of antennas, a substrate measurement device, and a selector. Each antenna in the plurality of antennas is configured to couple to a substrate layer primarily composed of biological tissue having at least one predetermined electrical property, and to enable an antenna/substrate combination to have an input impedance that enables radio energy at a predetermined range of frequencies to radiate from the antenna/substrate layer combination. One antenna in the plurality of antennas has a configuration that enables the one antenna and the substrate layer to emit radio energy through tissue covered by the substrate. The substrate measurement device is configured to identify the at least one predetermined electrical property of the substrate. The selector is configured to select the one antenna from the plurality of antennas for coupling with the substrate.

DETAILED DESCRIPTION

Medical imaging devices generate images corresponding to various types of biological tissue. Such tissue includes, but is not limited to, skin, bones, muscles, adipose, cartilage, tendons, cysts, growths, and tumors. The tissue may belong to an animal including humans, or to plants and other organisms. The imaging may be performed on biological tissue of a living or deceased organism. The term "skin" as used herein may refer to human skin or the skin of an animal. Skin may also be more generic, referring to the outermost layer of biological tissue of an organism that undergoing medical imaging.

As used herein, the term "radiator" refers to a structure in an antenna that emits electromagnetic energy when an electrical signal is applied to the radiator. The term "feed" refers to an electrically conductive structure in an antenna that couples a source of an electrical signal, such as a signal generator providing an electrical signal through an electrically conductive wire, to the radiator. As used herein, the term "via" refers to any electrical conductor that establishes an electrical connection between two different electrical conductors that are positioned approximately parallel to one another.

Figure 1A:
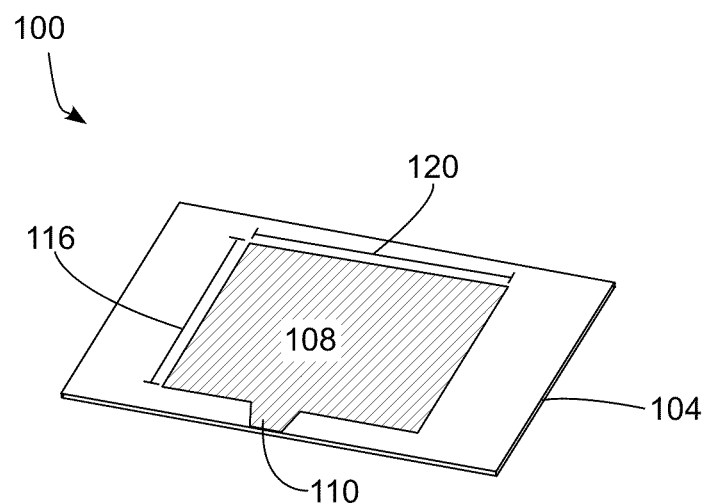
FIG. 1A is a perspective view of a patch antenna suitable for transmitting microwave energy when placed in contact with skin.
Figure 1B:
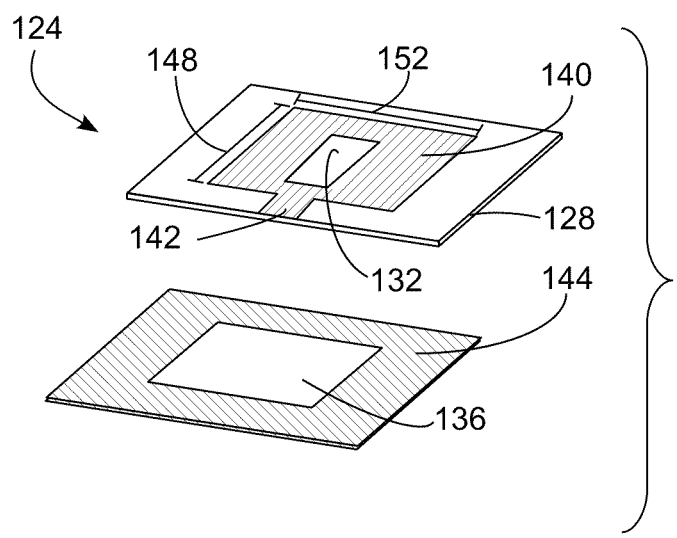
FIG. 1B is a partially exploded perspective view of another embodiment of a patch antenna suitable for transmitting microwave energy when placed in contact with skin.
Figure 1C:
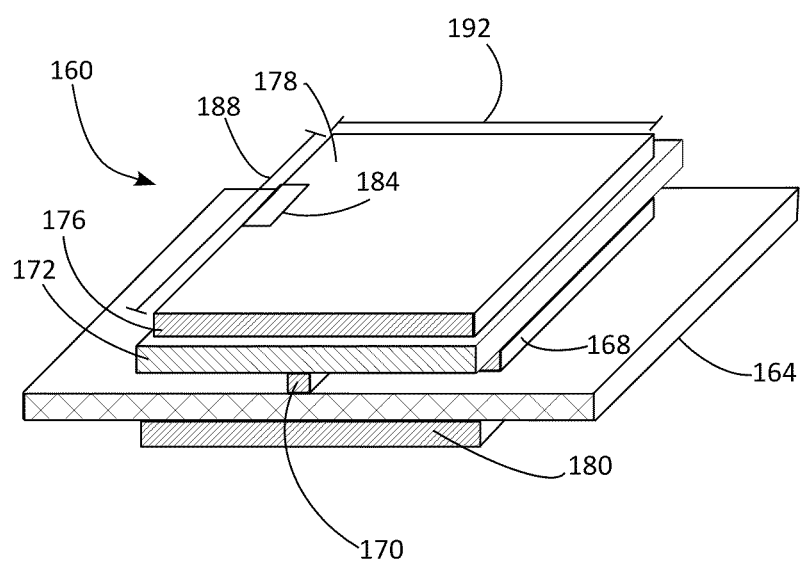
FIG. 1C is a perspective view of still another patch antenna suitable for transmitting microwave energy when placed in contact with skin.

Patch antennas configured to transmit microwave energy through human skin are depicted in FIG. 1A, FIG. 1B, and FIG. 1C. In FIG. 1A antenna 100 is a rectangular microstrip antenna including a radiator 108 of length 116 and width 120, feed 110, and adhesive backing 104. In the example of FIG. 1A, antenna 100 is primarily composed of a flexible, copper-clad material such as Pyralux. The copper surface of radiator 108 is exposed in order to be placed in contact with the surface of the skin of a test subject. Feed 110 provides an interface for connection of lead wires that electrically connect antenna 100 to a microwave signal generator (not shown). Adhesive backing 104 provides an adhesive area that adheres to the skin of a patient, maintaining contact between radiator 108 and the skin. In one embodiment, the radiator 108 bends into a curved shape when adhered to the skin to conform to the shape of the breast during operation. When adhered to the skin, antenna 100 is held in a stable position relative to the underlying tissue being imaged.

Antenna 100 is tuned to resonate at a desired frequency and impedance when placed in contact with skin. In the example of FIG. 1A, antenna 100 is tuned to a primary frequency of 2.45 GHz with a 50 Ωimpedance when it is placed in contact with human skin. While this frequency and impedance setting is an example of a configuration found to be effective in microwave imaging of human breast tissue, alternative frequencies and impedances are be employed in different imaging system embodiments. Because human skin has electrical properties including conductance and a dielectric coefficient, antenna 100 does not operate at the tuned frequency if it transmits microwave energy when separated from the surface of the skin. A method for adjusting antenna 100 to operate at the desired frequency and impedance when in contact with skin is described in more detail below. Once tuned, antenna 100 is coupled to a microwave signal generator by feed 110, and antenna 100 is able to emit a continuous microwave signal, or modulated microwave signals generated by the microwave signal generator.

FIG. 1B depicts another embodiment of a microstrip antenna 124 including a radiator 140 having a length 148 and width 152, feed 142, an electrically non-conductive adhesive backing 128, a slot 132 formed through the radiator 140, and another slot 136 formed through an electrical ground layer 144. Slots 132 and 136 each have a length and width that are adjusted to tune the antenna 124. In the example of FIG. 1B, antenna 124 is primarily composed of a flexible, copper-clad material, such as Pyralux. The copper surface of radiator 140 is exposed in order to be placed in contact with the surface of the skin of a test subject. Feed 142 provides an interface for connection of lead wires that electrically connect antenna 124 to a microwave signal generator (not shown). Adhesive backing 128 provides an adhesive area that adheres to the skin of a patient, maintaining contact between radiator 140 and the skin. The adhesive backing 128 is formed from an electrically non-conductive material that separates the radiator 140 from the ground layer 144.

As described in more detail below, antenna 124 is tuned to a selected primary frequency and impedance. In the example of FIG. 1B, antenna 124 is tuned to a primary frequency of 2.45 GHz with a 50Ω impedance when it is placed in contact with human skin. In one embodiment, the radiator 140 bends into a curved shape when adhered to the skin to conform to the shape of the breast during operation. When adhered to the skin using adhesive backing 128, antenna 124 is held in a stable position relative to the underlying tissue being imaged.

FIG. 1C depicts a third a microstrip antenna embodiment 160. The microstrip antenna 160 includes a radiator 168 having a feed 170, electrically non-conductive adhesive backing 164, electrical ground layer 180, an electrically conductive top layer 176, dielectric layer 172, and an electrical short 184. In the example of FIG. 1C, antenna 160 is primarily composed of a flexible, copper-clad material, such as Pyralux. The radiator 168 has a shape similar to radiators 108 and 140 as depicted in FIG. 1A and FIG. 1B, respectively. The top conductor 176 has a length 188, a width 192, and includes a copper surface 178. The copper surface 178 is exposed in order to be placed in contact with the surface of the skin of a test subject. Electrical short 184 is depicted as a via that establishes an electrical connection between the top conductive layer 176 and the ground 180. Thus, the top conductive layer 176 is also an electrical ground. Feed 170 provides an interface for connection of lead wires that electrically connects the radiator 168 to a microwave signal generator (not shown).

As described in more detail below, antenna 160 is tuned to a selected primary frequency and impedance. In the example of FIG. 1C, antenna 160 is tuned to a primary frequency of 2.45 GHz with a 50Ω impedance when it is placed in contact with human skin. In one embodiment, the antenna 160 bends into a curved shape when adhered to the skin to conform to the shape of the breast during operation. When adhered to the skin using adhesive backing 164, the antenna 160 is held in a stable position relative to the underlying tissue being imaged.

While the embodiments of FIG. 1A-FIG. 1C depict antenna configurations having rectangular radiators, various different antenna configurations include radiators having different shapes including ellipsoidal, curved, and polygonal shapes, as well as ground layers and dielectric layers having different shapes. The sizes, shapes, positions, and selected materials used in the various structures in each of the antennas 100, 124, and 160 are selected to tune the antennas to a selected resonant frequency, impedance, and radiation pattern for tissue imaging.

Figure 2A:
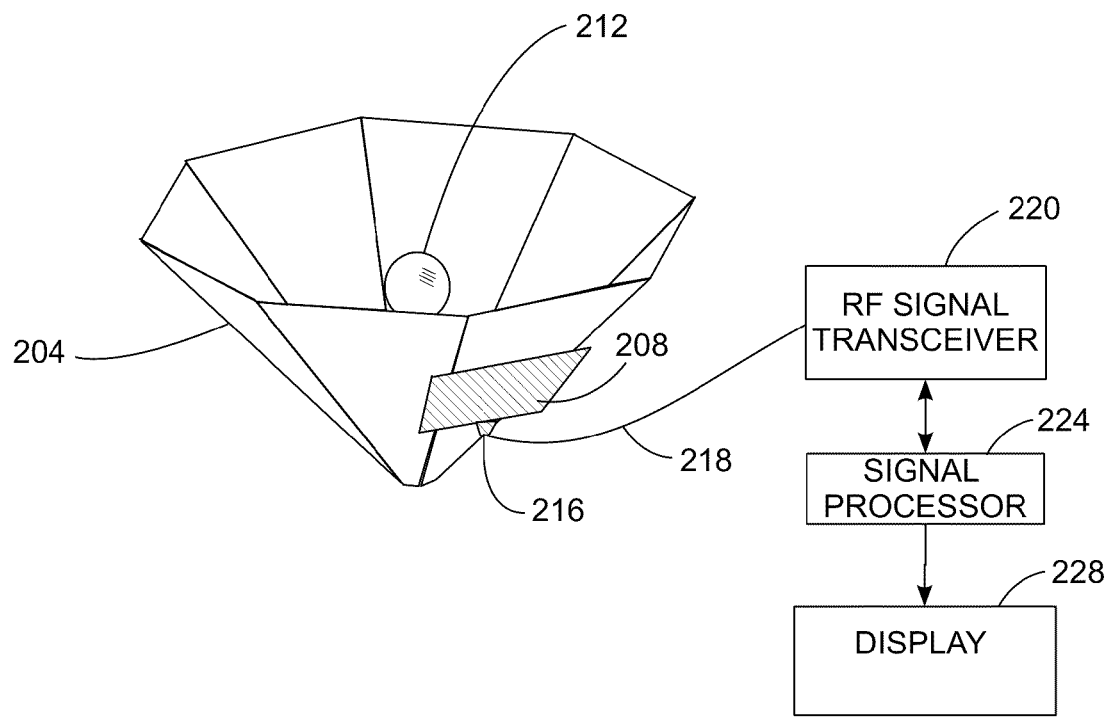
FIG. 2A is an illustration of a model of a human breast with the antenna of FIG. 1 placed in contact with the breast.

FIG. 2A depicts the patch antenna of FIG. 1A, FIG. 1B, or FIG. 1C in contact with the surface of model of a human breast. FIG. 2A shows a model 204 of a human breast in a conical form that is 10 cm in width and 5 cm in height with sides divided into eight facets. Antenna 208 is a patch antenna tuned to transmit microwave energy when placed in contact with the surface of model 204. The radiator of antenna 208 is placed in contact with the surface of model 204. The interior of model 204 includes an example of a tumor 212 that is modeled as a sphere having a diameter of 1 cm. The outer layer of model 204 includes a skin that is 2 mm in thickness.

The antenna 208 is electrically connected to a radio frequency (RF) transceiver 220 through an electrically conductive cable or wire 218 that is connected to antenna feed 216 and the RF transceiver 220. The RF transceiver 220 includes a transmitter that generates electrical signals for the antenna 208 to emit as electromagnetic signals, and a receiver that detects electrical signals that correspond to radio frequency signals received by the antenna 208. The signal generator in the RF transceiver 220 has an output impedance that corresponds to the input impedance of a combination of antenna 208 and the skin on the model 204 when the antenna 208 is coupled to the model 204. In the example of FIG. 2A, the RF transceiver 220 generates and detects RF signals in the microwave band, although alternative RF transceivers send and receive in different frequency ranges. In another embodiment, a separate RF transmitter and RF receiver are electrically connected to the antenna 208. While FIG. 2A depicts a single antenna connected to the RF transceiver 220, two or more antennas are placed in contact with the breast 204 at different locations and are connected to the RF transceiver in alternative configurations.

When antenna 208 is positioned in contact with the skin covering the breast tissue and tumor, microwave energy emitted through antenna 208 penetrates the skin and travels through surrounding breast tissue until reaching the surface of tumor 212. Tumor 212 causes some of the microwave energy to scatter. A portion of this scattered microwave energy returns through the surface of model 204. The antenna 208 and transceiver 220 detect the scattered microwave energy. A signal processor 224 is configured to generate a visual depiction of the tissue in the breast 204 and tumor 212. In some configurations, the signal processor 224 also generates command signals to operate the RF transceiver 220. Signal processor 224 includes a processor such as a central processing unit (CPU), graphical processing unit (GPU), digital signal process (DSP) or other suitable components and computer programs that enable the signal processor to generate two-dimensional and three-dimensional visualizations of the breast tissue 204 and tumor 212. A display 228, such as an LCD display or the like, is connected to the signal processor 224 and displays the two or three dimensional visualizations generated by the signal processor 224.

Figure 3A:
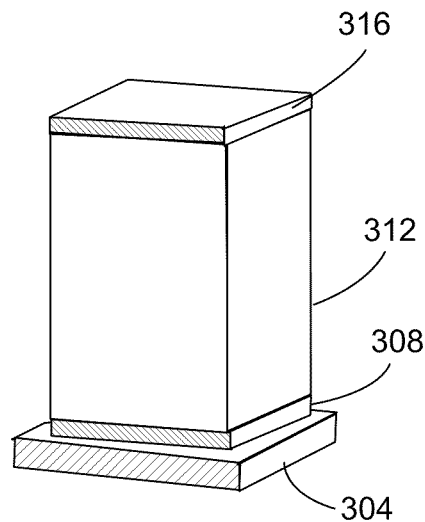
FIG. 3A is a perspective view of an antenna such as the antennas in FIG. 1A-FIG. 1C that is positioned to transmit microwave energy through layers of breast tissue.

A cross-sectional view of breast tissue through which the microwave energy travels is seen in FIG. 3A, with antenna 304 placed in contact with a first skin layer 308. The first skin layer 308 acts as a substrate with the antenna 304, and the coupled skin layer 308 and antenna 304 radiate radio energy into the breast tissue 312. Healthy breast tissue 312 is composed of fatty tissue, which may contain one or more structures, such as muscles, glands, cysts or tumors, that separate layer 308 from a second skin layer 316.

Figure 3B:
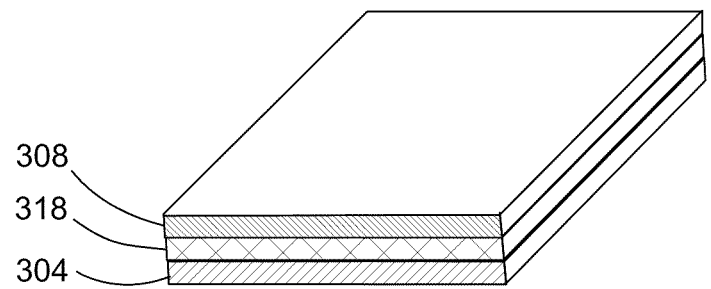
FIG. 3B is a perspective view of an antenna such as the antennas in FIG. 1A-FIG. 1C that is covered by a signal enhancing and/or comforting material and is configured to transmit microwave energy through layers of breast tissue.

FIG. 3B, depicts an alternate configuration for coupling antenna 304 to the breast skin 308 through a layer of signal enhancing or comforting material 318. The signal enhancing or comfort material 318 provides comfort to the patient wearing the antenna 304, while also having selected electrical properties that are similar to the breast skin 308 to enhance propagation of radio signals into the breast tissue 312. Signal enhancing or comforting materials have electrical properties that are similar to the skin layer 308, such as a dielectric permittivity of approximately 40. In some configurations, the signal enhancing materials also have an electrical conductivity that is similar to the skin layer 308, such as a conductivity of approximately 1.1 S/m. Materials that are suitable to provide signal enhancement and comfort include polymers, silicone, flexible glass fibers, flexible ceramic fibers, cloths, and foams, such as Polyurethane foam. Various embodiments of signal enhancing or comforting material 318 are in the form of a tape or adhesive material to enhance contact with the skin layer 308. The signal enhancing or comforting material 318 conforms to the shape of a breast or other portion of the body to improve contact with the skin 308 and be comfortable to wear. Some commercially available brassiere products include suitable signal enhancing or comforting materials, or may be fitted with signal enhancing or comforting materials for use with the antenna 304.

Figure 4A:
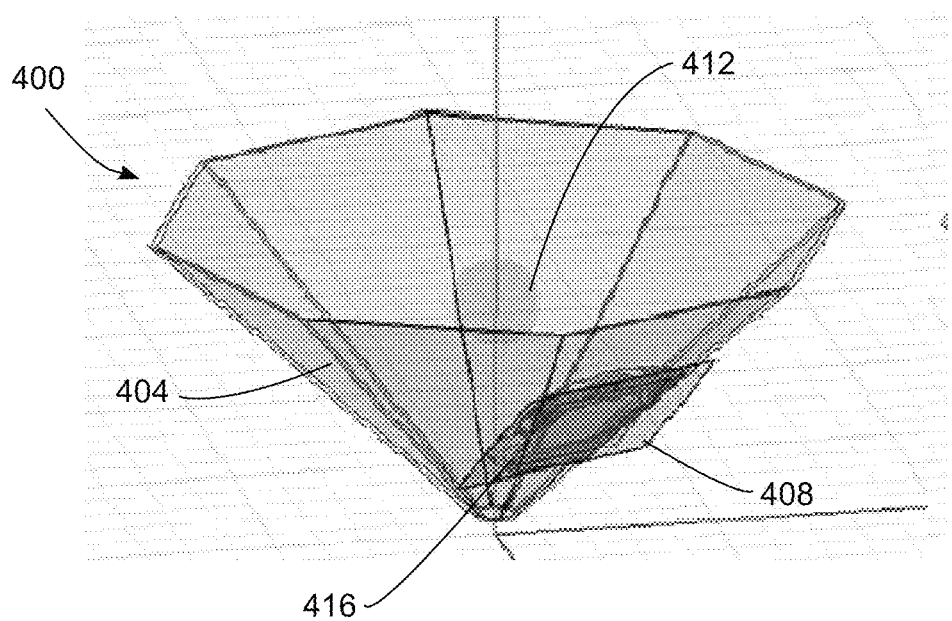
FIG. 4A is an illustration of a model of a human breast with the antenna of FIG. 1 showing the current density pattern of microwave energy in the skin.

An illustration depicting microwave energy reflected from the skin of a breast model using the antennas of FIG. 1 is depicted in FIG. 4A. FIG. 4A uses breast model 404, which has the same configuration as the breast model of FIG. 2A. Antenna 408 is similarly placed in contacted with the skin on the surface of model 404. Contour lines 416 surrounding the center of antenna 408 indicate the current density of electrical currents induced in the skin of model 404. Areas with a higher measured current density indicate that microwave energy emitted by antenna 408 is being reflected by the skin of model 404. The reflected energy depicted by contour lines 416 is localized to the periphery of the antenna, with the greater portion of the emitted energy entering the breast tissue and traveling towards tumor 412. This emission pattern occurs because the skin of breast model 404 acts as a substrate layer of antenna 408 when antenna 408 is placed in contact with the breast skin. The combination of antenna 408 and skin on the breast model 404 emit a greater portion of the radio energy into the breast tissue within model 404 than the prior art antenna.

Figure 4B:
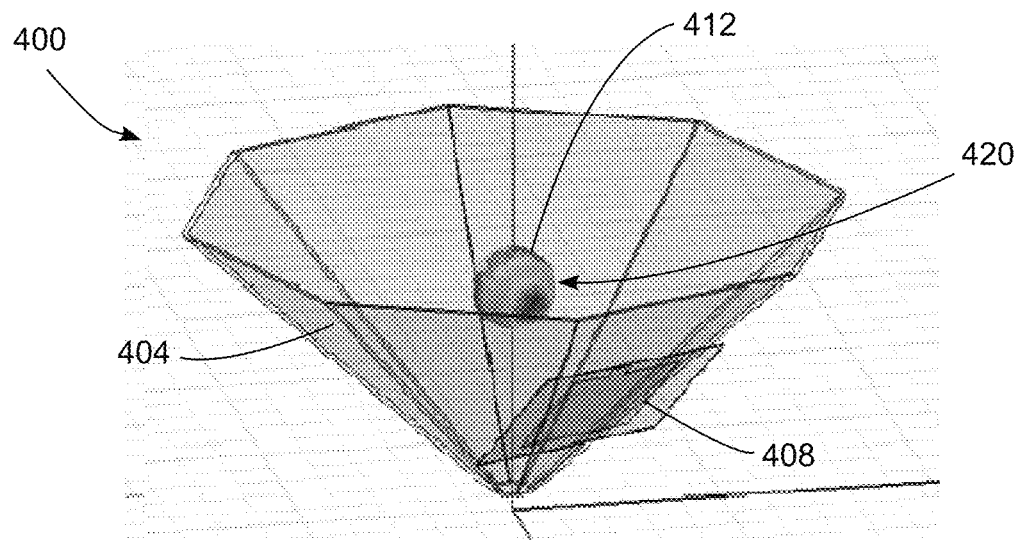
FIG. 4B is an illustration of the model and antenna of FIG. 4A showing the current density pattern of microwave energy in a tumor.
Figure 9:
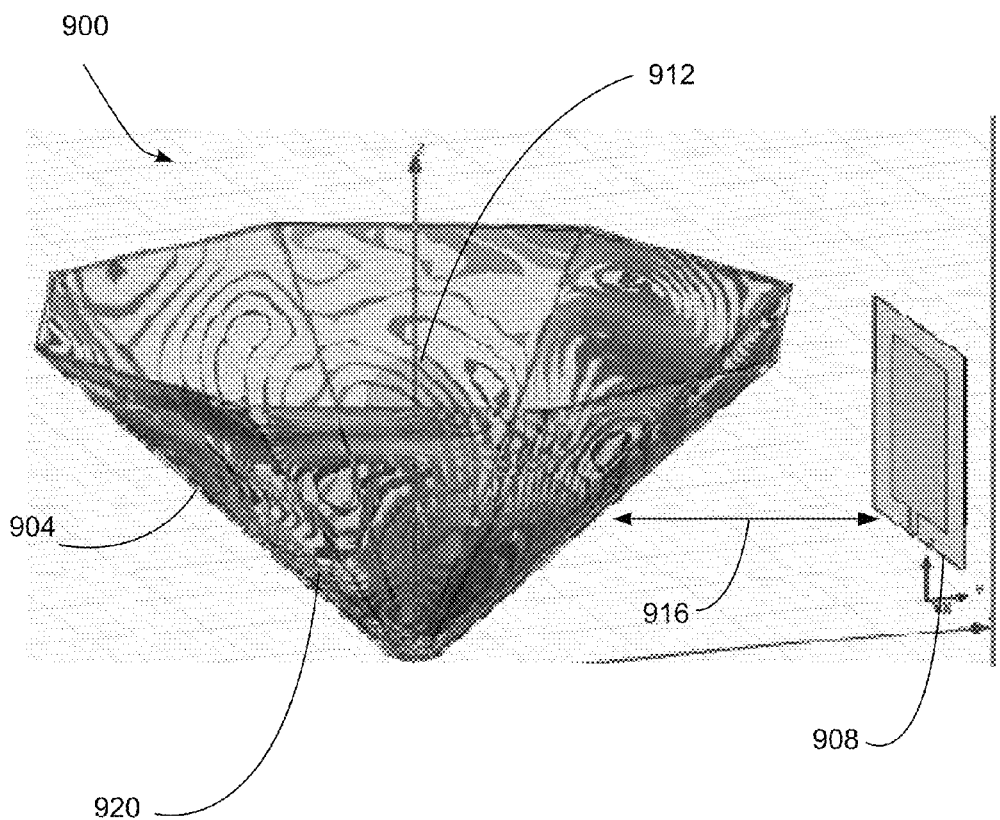
FIG. 9 is an illustration of a model of a human breast with a prior art antenna showing the current density pattern of microwave energy in the skin.

In FIG. 4B, reflected microwave energy is minimized because the breast skin itself becomes an emitting element instead of a passive reflective element. The results of FIG. 4A are contrasted with a prior art antenna arrangement seen in FIG. 9. In FIG. 9, antenna 908 is placed at a predetermined distance 916 from the surface of breast model 904. In the example of FIG. 9, distance 916 is 5 cm. Antenna 908 may emit the same microwave energy as antenna 408, but the skin on model 904 reflects a substantial portion of the microwave energy. The contour lines 920 that cover each facet of the surface of model 904 show the induced current density over the entire surface of model 904, indicating a large amount of reflected microwave energy. The reflected energy is unable to penetrate the model, and it acts as a noise source, obscuring reflected energy from tumor 912. If prior art antenna 908 is placed in contact with the surface of model 904, the electrical properties of the skin covering 904 interfere with operation of the prior art antenna, preventing it from operating at the desired frequency. These electrical properties include the electrical conductivity and dielectric permittivity of the skin.

FIG. 4B depicts the same model 404 and antenna 408 of FIG. 4A. In this illustration, contour lines 420 on the surface of tumor 412 indicate the density of an electrical current induced in the surface of tumor 412. As discussed above, the current density indicates that microwave energy is reaching and reflecting off of tumor 412 through the skin and surrounding breast tissue. An example of the maximum strength of an induced current density using the example embodiment of FIG. 4B is 69.65 A/m$^2$.

Figure 5:
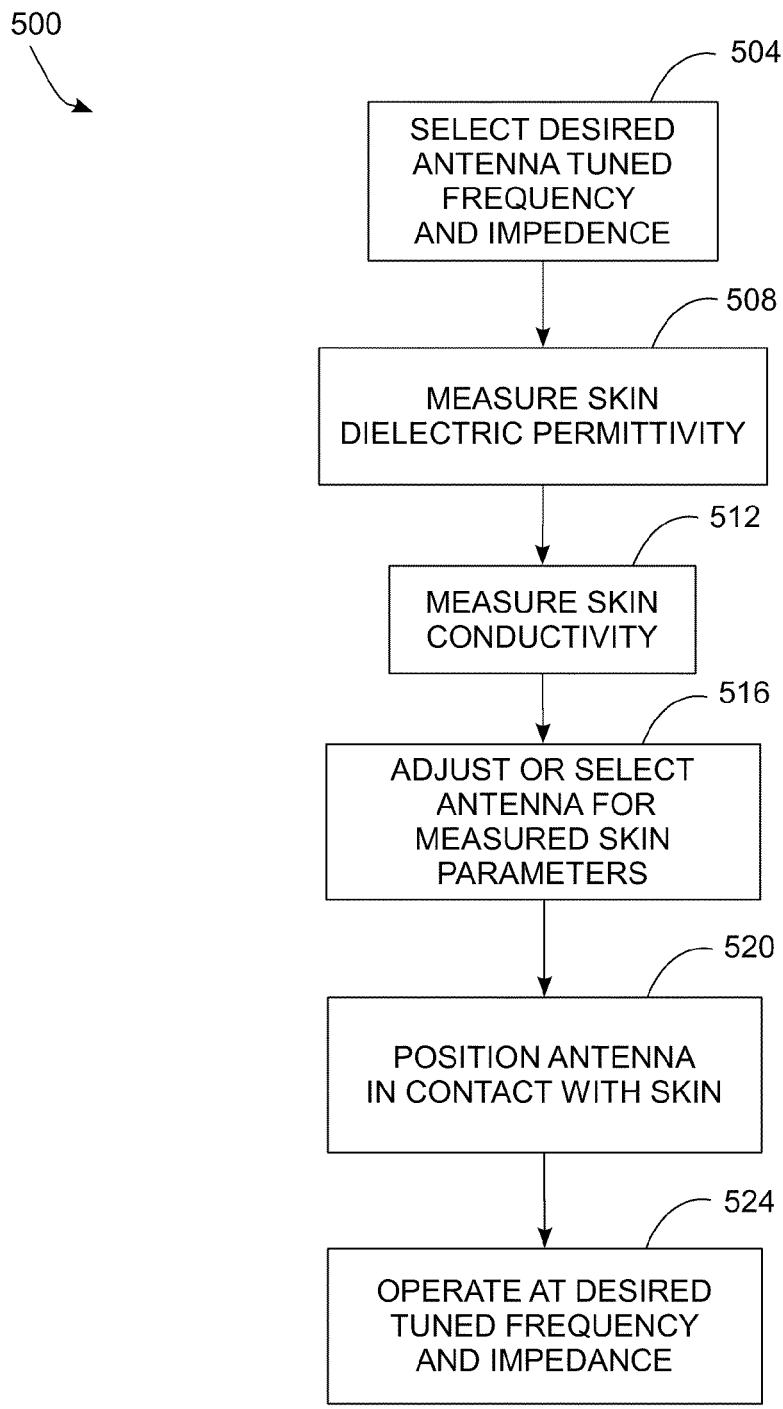
FIG. 5 is a flow diagram of a method for adjusting the antenna of FIG. 1 to operate at a desired frequency when placed in contact with human skin.

A process 500 for adjusting an antenna to operate at a desired resonant frequency when placed in contact with skin is shown in FIG. 5. First, the final desired resonant frequency and input impedance for the antenna when placed in contact with skin are determined (block 504). The desired resonant frequency may change depending upon the type of material being imaged. The desired input impedance may be selected to match the output impedance of a microwave signal generator to prevent signal reflection from the antenna to the generator.

Figure 2B:
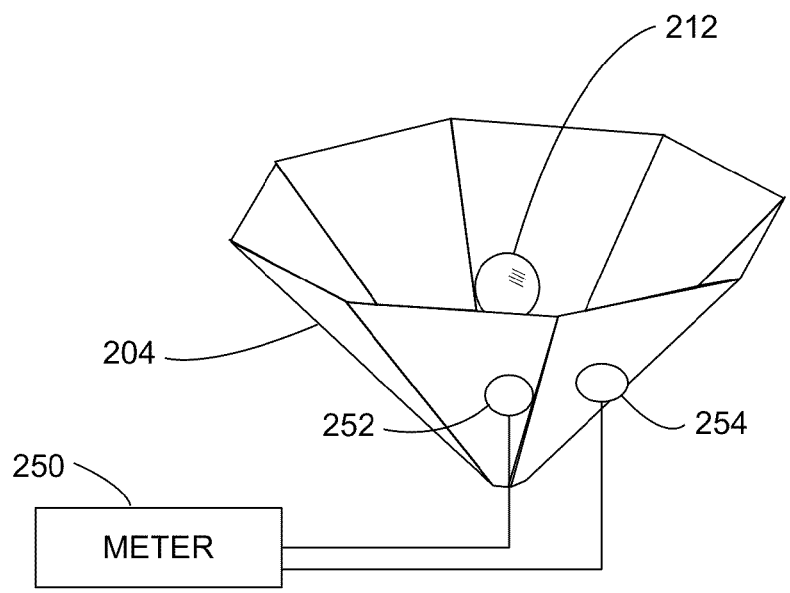
FIG. 2B is an illustration of the model of the human breast from FIG. 2A with a measurement device electrically connected to skin on the model.

Next, one or more electrical properties of the skin being coupled to the antenna are measured. The dielectric constant of permittivity in the skin is measured using a known method such as measuring the capacitance of the skin using a multimeter and identifying the dielectric constant from the capacitance and thickness of the skin (block 508). A dielectric constant of approximately 40 is typical for human skin, although the measured result may vary based on various factors affecting the condition of the skin. The electrical conductivity of the skin is also measured (block 512) using a measurement device such as an ohmmeter. In human skin, a measured conductivity on the order of 1.1 S/m is typical, although this value may also vary based on the condition of the skin. As seen in FIG. 2B, a meter 250, such as an ohmmeter or multimeter, is electrically coupled to a breast model 204 using electrodes 252 and 254. The meter 250 measures various electrical properties of the skin on the breast 204 model, including conductance and capacitance. The electrical properties of the skin are identified based on the measurements generated by the meter 250.

After measuring the electrical characteristics of the skin, the emitter element of the antenna is adjusted so that the combined antenna and skin emit microwave energy at the desired resonant frequency and input impedance (block 516). The resonant frequency of the antenna may be adjusted by increasing or decreasing length and/or width of the radiator, such as radiators 108, 140, and 168 depicted in FIG. 1A, FIG. 1B, and FIG. 1C, respectively. For example, if the resonant frequency of the antenna is higher than the desired frequency, the length of the radiator is increased and vice versa. The input impedance of the antenna may be adjusted by changing the position of the feed and/or increasing or decreasing the width of the radiator. The input impedance of the antenna may be increased by moving the feed away from the center of the corresponding radiator towards one corner of the radiator and/or by decreasing the width of the radiator. A transformer, such a balun, may be electrically connected between the antenna and the microwave signal generator to provide a tunable input impedance for the antenna when placed in contact with skin and the output impedance of the microwave signal generator.

The embodiments of FIG. 1B and FIG. 1C may be adjusted to a selected frequency, an input impedance, and a radiation pattern by altering the length and width of the radiator, position of the feed, and by adjusting other structures in the antenna. For example, in the embodiment of antenna 124 shown in FIG. 1B, the length, width, surface area, and position of the slots 132 and 136 are adjusted to tune the antenna to a desired frequency, input impedance, and radiation pattern. In the embodiment of antenna 160 shown in FIG. 1C, the length 188 and width 192 of the top conductor 176 and the size and location of the via 184 is adjusted to tune the antenna 160 to a desired frequency, input impedance, and radiation pattern.

As seen in FIG. 1A-FIG. 1C, antennas 100, 124, and 160 may be manufactured with various different sizes and configurations of structures in each antenna for a range of input impedance, resonant frequency, and radiation pattern parameters. In one configuration, a pre-fabricated antenna is selected from a plurality of differently configured pre-fabricated antenna types. The selected antenna has the desired input impedance, resonant frequency, and radiation pattern parameters when coupled to the skin for tissue imaging. The selection of the antenna is made after measuring the electrical and physical properties of the skin, such as the dielectric permittivity and electrical conductivity of the skin.

The plurality of antennas each include variations to the structures in the antenna that enable different antenna characteristics including resonant frequency and input impedance when coupled with skin. For example, variations of antenna 100 include a range of widths 120 for the radiator 108, and various different positions of the feed 110 with respect to the radiator 108. Variations of antenna 124 further include different sizes and positions of the slots 132 and 136. Variations of antenna 160 further include different sizes of the top conductor 176 and different connection positions of the via 184. In some embodiments, multiple antennas are coupled to the skin. Each of the antennas that are coupled to the skin have the selected antenna structure.

In one example, the selected characteristics of an antenna coupled to the skin include a 2.45 GHz resonant frequency and an input impedance of 50Ω. The skin is measured with a conductivity of 1.1 S/m, and a dielectric constant of 40. In some configurations, some or all of the electrical properties of the skin are estimated instead of being measured directly. An antenna is selected from a group of differently configured antennas that each have a configuration that produces the selected resonant frequency and input impedance when coupled to the skin. One antenna is selected that is configured to emit radio waves at the selected 2.45 GHz frequency and 50Ω input impedance when the antenna is coupled to skin having the measured conductivity of 1.1 S/m and dielectric constant of 40 in the skin. An operator may select an appropriate antenna using a reference table, computer program, or any device that correlates the measured skin parameters to a selected set of antenna parameters.

Selection of a suitable antenna from a group of pre-fabricated antennas eliminates the need to adjust a single antenna by cutting or otherwise altering structures in the antenna. A pre-fabricated antenna is identified based on the relationship between measured properties of the skin, and selected antenna parameters such as the resonant frequency and input impedance. Each pre-fabricated antenna is configured to operate over a predetermined range of resonant frequencies, and input impedances for a predetermined range of skin properties.

After the antenna is selected or configured to operate at the desired resonant frequency, it is placed in contact with the skin of a test subject (block 520). This may include cleaning the area under the antenna to promote a uniform electrical contact. The placement may additionally include application of a moisturizing lotion or a topical cream to the area of skin placed in contact with the antenna. The application of this lotion or cream may enhance the electrical contact between the antenna and the underlying skin layer. The topical cream may also include an electrically conductive gel that promotes electrical contact with the skin, such as commercially available gels used for affixing electrodes to human skin. An adhesive backing may also be used to ensure that the antenna remains in the same relative position on the patient during the microwave imaging process. Alternatively, a layer of additional material is used on the antenna that contacts the skin. The additional layer enhances the microwave signal penetration through the skin or the comfort to the patients or both.

Once the antenna is configured and attached to the patient's skin, the microwave signal generator may operate at the desired frequency and impedance (block 524). The antenna emits microwaves that pass through the skin and into tissue layers such as breast tissue. Other structures in the breast tissue including tumors reflect the microwave energy. The backscatter of microwave energy may be detected in order to identify possible tumors disposed in the breast tissue. Detected microwave energy may be received by one or more receiver antennae, be processed by a signal processor such as signal processor 224 seen in FIG. 2A, and be displayed on an imaging device such as display 228.

Figure 6:
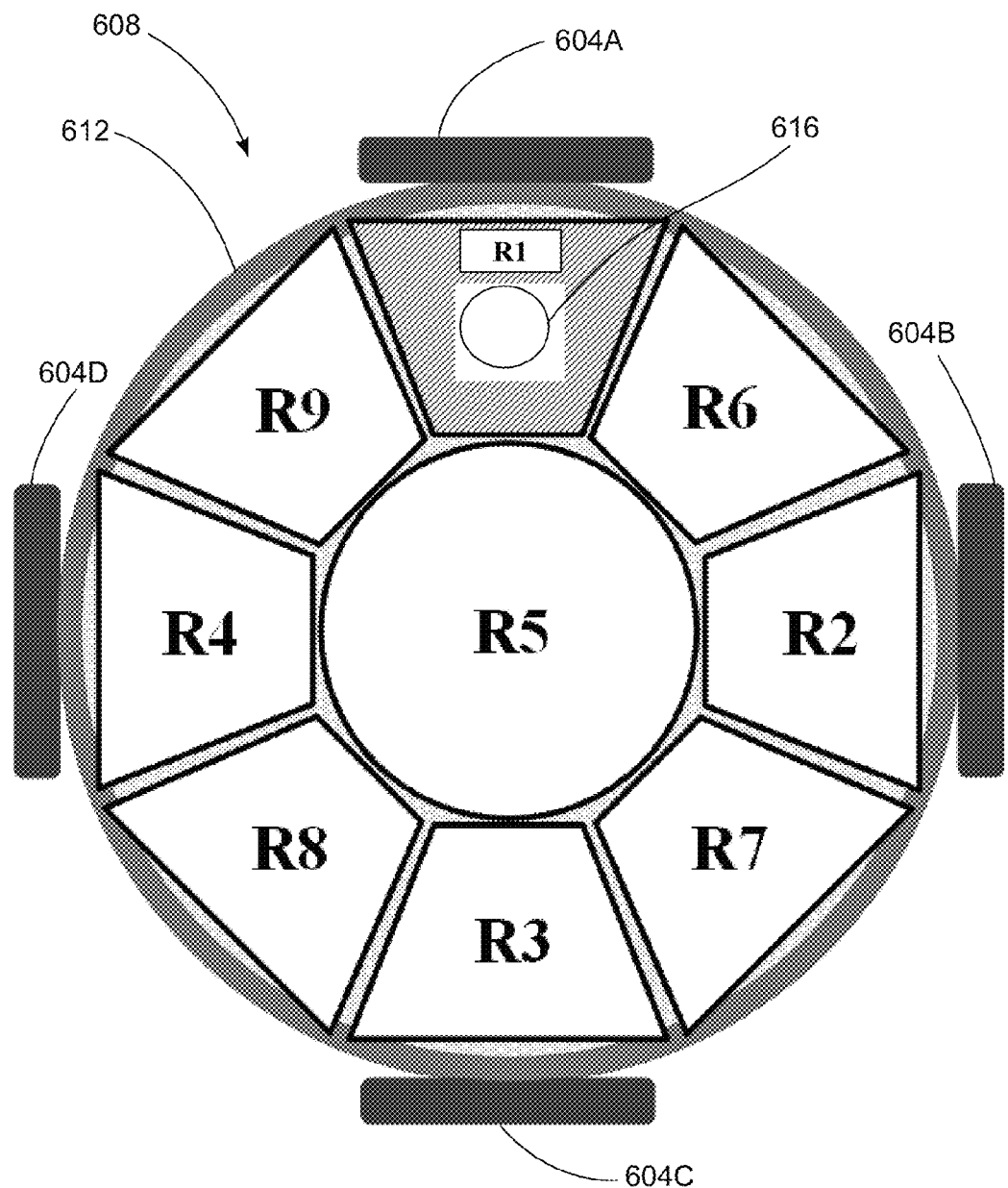
FIG. 6 is a schematic view that depicts four antennas positioned about a breast and regions within the breast tissue.

FIG. 6 depicts four microstrip antennas 604A-604D positioned around a breast 608 in contact with skin 612. The antennas 604A-604D may be incorporated in a garment, such as the single breast cup 700 depicted below in FIG. 7, that is fitted to the breast 608. The antennas 604A-604D may have the same structure, tuning, and impedance as microstrip antennas 100, 124, and 160 from FIG. 1A-FIG. 1C.

In FIG. 6, the interior of the breast 608 is divided into regions R1-R9. The breast 608 contains a tumor 616 located in a region R1. The arrangement of antennas 604A-604D may detect both the position and the size of the tumor 616. In operation, one of the antennas, such as antenna 604A, emits a signal that is directed into the tissue of breast 608. In the example of FIG. 6, the signal is emitted in a microwave frequency range of 2.1 GHz-2.5 GHz, although alternative signals may use different frequency ranges. As the signal propagates through the breast 608, various tissues in the breast, including the tumor 616, scatter and attenuate the signal. The tumor 616 has a higher water content than the surrounding tissue in the breast 608, and the water in the tumor 616 scatters the signal to a greater degree than the surrounding tissue. Each of the antennas 604A-604D are configured to receive the scattered signal, including a backscatter signal reflected from the tumor 616 and detected by antenna 604A. The breast tissue absorbs a portion of the energy in the scattered signal emitted by the antenna 604A, which may be referred to as a "scatter loss." The antennas 604A-604D may be calibrated using simulated breast material, such as glycerine, to identify signal noise and scatter loss that occur in healthy breast tissue prior to testing breast tissue that may include tumors.

To detect and identify the position of a tumor in the breast 608, antenna 604 emits a signal through the skin 612 into the tissue in breast 608. The signal scatters as the signal propagates through the breast tissue, and antennas 604A-604D record the scattered signal. In the example of FIG. 6, the signal encounters the tumor 616 in region R1. The tumor 616 scatters the signal emitted from the antenna 604A to a greater degree than normal breast tissue, resulting in a larger magnitude of backscatter radiation detected by the antenna 604A. Each of the antennas 604B-604D emit a signal in a similar manner with the remaining antennas detecting the scattered signal. Due to the position of the tumor 616 proximate to antenna 604A, the greatest magnitude of backscatter radiation is detected at antenna 604A. Antennas 604B and 604D are each positioned at approximately equal distances from the tumor 616 and each receive backscatter signals having roughly equal magnitudes. The antenna 604C is farthest from the tumor 616 and receives a backscatter signal having a magnitude that is lower than the magnitude of backscatter signals received by the other antennas 604A, 604B, and 604D.

The position of the tumor may be identified using the relative magnitudes of backscatter signal detected at each of the antennas 604A-604D. In the example of FIG. 6, the highest backscatter signal strength occurs near antenna 604A, with equal strength backscatter signals detected by antennas 604B and 604D indicating that the tumor 616 is located in region R1. Further, in some embodiments, existing signal conditioning methods are applied to the received backscatter signal. In these embodiments, the signal is fed to existing image reconstruction computer programs, which use existing image reconstruction algorithms to generate two dimensional and three dimensional images of the breast. These images show different parts of the breast, some of which may include tumors. While FIG. 6 depicts four antennas positioned on the breast 608, alternative embodiments may include more antennas around the breast 608. Additional antennas enable measurement of the position of tumors in the breast over a greater number of regions in the breast, increasing the precision of identification of the position of tumors in the breast tissue.

The antenna configuration of FIG. 6 may also estimate the size of a tumor in the breast using the measured scatter return signal. The amplitude of the measured scatter return signal increases as the size of a tumor, such as tumor 616, increases. In the embodiment of FIG. 6, the magnitude of detected backscatter for a signal emitted through healthy breast tissue is approximately −56 decibels (dB). This value may be identified by calibrating the antennas 604A-604D using healthy breast tissue or glycerine as described above. When antenna 604A emits a signal proximate to the tumor 616, the magnitude of the detected backscatter signal increases. If tumor 616 has a diameter of 5 mm, the measured scatter loss is −47 dB, while the measured scatter loss for tumor 616 is −38 dB when the diameter of the tumor is 7.5 mm. Note that the magnitude of backscatter signal increases as the decibel number approaches zero, so the −38 dB signal for the 7.5 mm tumor represents the largest magnitude of detected backscatter, while the −56 dB measured loss for healthy breast tissue is the smallest magnitude of detected backscatter. Using empirical calibrations for known tumor sizes, the antenna arrangement depicted in FIG. 6 may identify tumors of various sizes in the breast 608. Both the size and position of a detected tumor may be display visually using a display device such as an LCD display the display a model of the breast tissue and tumor. Using various visualization techniques, the display depicts a two dimensional or three dimensional representation of the breast tissue and tumor.

Figure 7:
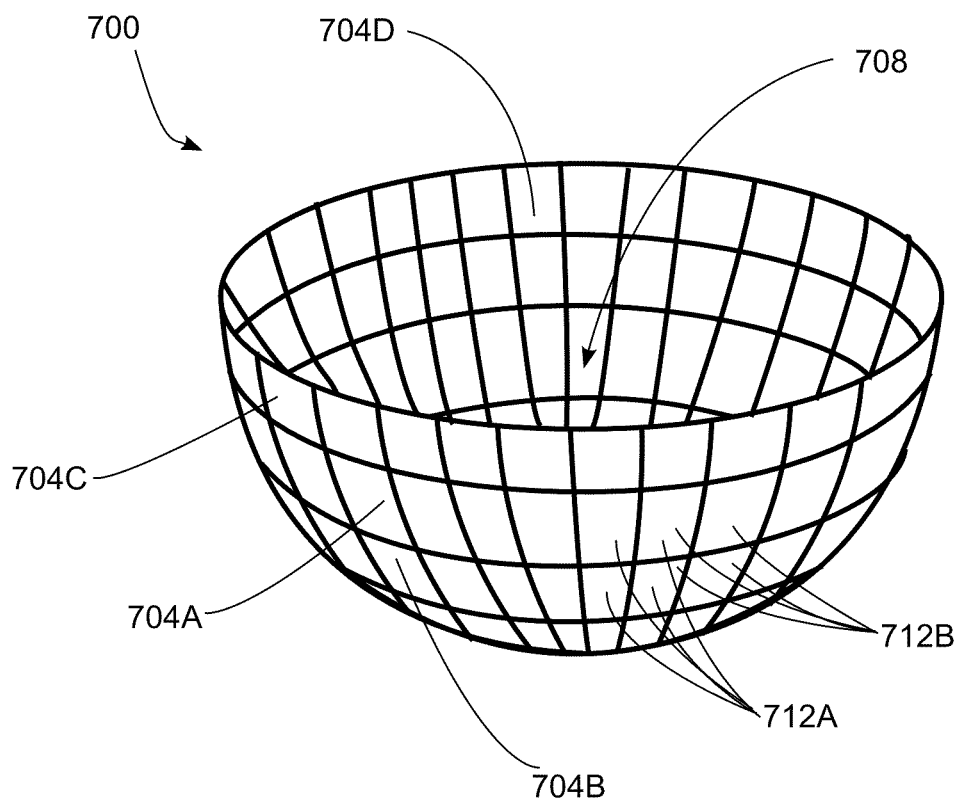
FIG. 7 is a perspective view of an arrangement of a patch antenna arranged in a wearable garment adapted to be worn on a breast.

An arrangement of patch antennae suitable to be worn on a human breast is depicted in FIG. 7. A breast cup 700 is formed including multiple antennae shaped to fit the outer wall of the breast cup 700, such as antennae 704A-704D. The cup is formed with an inner cavity 708 that may be adapted to a variety of sizes and shapes to comfortably accommodate a breast. The radiators of each of the antennae are exposed to the inner cavity, as exemplified by the radiator of antenna 704D. Each of the radiators may contact the skin covering breast tissue. Breast cup 700 may hold the antennae in a fabric sheath with pockets arranged to hold an antenna in each pocket. This allows for individual antennae to be removed, adjusted, and then reinserted into breast cup 700. In the arrangement of FIG. 7, the multiple antennae of breast cup 700 are arranged to emit microwave energy into the breast from multiple sides of the breast and from multiple angles. Each antenna may receive backscatter microwave signals that reflect off structures in the breast tissue, including tumors.

Multiple antennae in breast cup 700 may be selectively activated in groups, and different antenna groups may be activated sequentially to scan the breast in three dimensions. Antenna group 712A includes four antennae placed in a two by two formation. Antenna group 712A may emit microwave signals from all four antennae simultaneously, and the other antennae in breast cup 700 may receive backscatter from those signals. Antenna group 712B is another group of four antennae, including two of the antennae from antenna group A. It may be activated at a different time from antenna group 712A to image the breast from a different angle. Selecting groups of smaller antennae such as groups 712A and 712B results in a higher image resolution than using a single antenna of a size equivalent to antenna groups 712A or 712B. By activating on or more antennae in a sequential manner, microwave energy may be sent into the breast tissue from multiple angles for imaging.

The single breast cup 700 of FIG. 7 may be paired with a second breast cup adapted for a second breast, and the two may be further held together in a brassiere that is worn by the test subject. Such an arrangement allows the antennae to remain in a fixed position relative to the breast tissue being imaged, and increases the comfort of the test subject. While FIG. 7 depicts a wearable breast cup, alternative garments adapted for use in imaging different portions of the body of a human or an animal are envisioned. For example, a circular waist-band garment could be used for imaging structures within the abdomen of a test subject.

Figure 8:
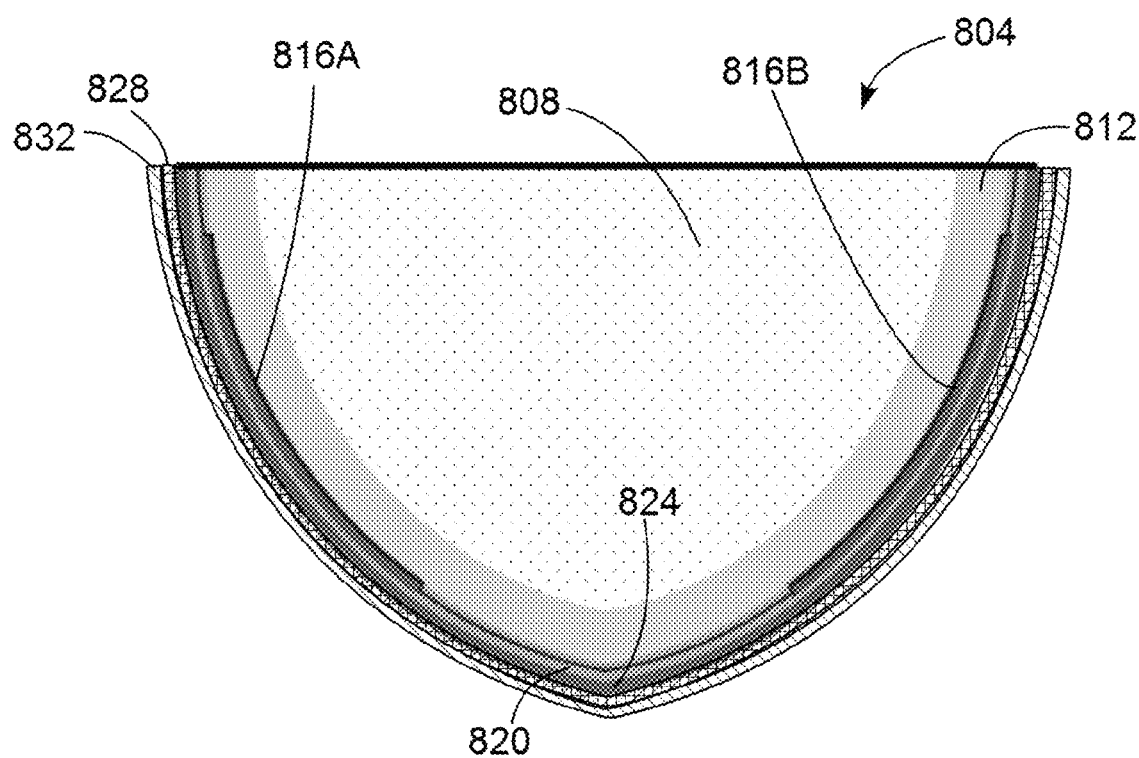
FIG. 8 is a cross-sectional view of structural elements in a wearable garment including antennas.

FIG. 8 depicts a cross-sectional view of an antenna array formed in a wearable garment that conforms to a breast, such as breast cup 700. A breast 804 includes a layer of skin 812 that encloses breast tissue 808. The antenna array includes antennas 816A and 816B, dielectric layer 820, and ground layer 824, and may include optional separator layer 828 and reflector layer 832.

The antenna array depicts two microstrip antenna elements 816A and 816B in cross section, although alternative configurations may include a different number and arrangement of antennas. The antenna elements 816A and 816B may be microstrip antennas as seen in FIG. 1A, FIG. 1B, and FIG. 1C. A dielectric layer 820 is positioned between the antenna elements 816A and 816B and a ground layer 824. The dielectric layer 820 is formed from an electrical insulator that resists a flow of electricity between the ground layer 824 and either of the antenna elements 816A and 816B. The dielectric layer 820 polarizes in the presence of an electrical field that is applied to the antenna elements 816A or 816B when emitting a signal into the breast 804. The ground layer 824 may be formed from a planar electrical conductor, such as copper, aluminum, or any other suitable electrically conductive material.

The embodiment of FIG. 8 includes an optional separator layer 828 formed over the ground layer 824 and a reflector layer 832 formed over the separator layer 828. Separator layer 824 is an electrical insulator, such as a polymer, that electrically isolates the reflector layer 832 from the ground layer 820. The reflector layer 832 is formed from a material that reflects radio energy frequencies emitted by the antenna elements 816A and 816B. In the example of FIG. 8, the reflector layer 832 is configured to reflect microwave energy in a frequency range of approximately 2 GHz-3 GHz emitted by the antenna elements 816A and 816B. The reflector layer 832 is formed from a material that reflects microwave energy, such as a sheet of copper or aluminum, that is shaped to conform to the separator layer 828. The separator layer 828 and reflector layer 832 are optional layers that reflect signals emitted by the antenna elements 816A and 816B into the breast tissue 808. The reflected signals improve the efficiency of operation of the antenna elements 816A and 816B.

Those skilled in the art will recognize that numerous modifications can be made to the specific implementations described above. For example, while the embodiments disclosed above are primarily directed towards the detection of tumors in breast tissue, the improved antenna and imaging techniques described herein are applicable to imaging many different structures in the bodies of humans, animals, and other organisms. Therefore, the following claims are not to be limited to the specific embodiments illustrated and described above. The claims, as originally presented and as they may be amended, encompass variations, alternatives, modifications, improvements, equivalents, and substantial equivalents of the embodiments and teachings disclosed herein, including those that are presently unforeseen or unappreciated, and that, for example, may arise from applicants/patentees and others.

We claim:

1. An antenna system comprising:
a plurality of antennas, each antenna in the plurality of antennas being formed with an input impedance, resonant frequency, and radiation pattern that differs from another input impedance, resonant frequency, and radiation pattern of each of the other antennas in the plurality of antennas in response to each antenna in the plurality of antennas being coupled to a substrate layer primarily composed of biological tissue having at least one predetermined electrical property to enable each antenna in the plurality of antennas to emit radio energy through tissue covered by the substrate layer, each antenna in the plurality of antennas comprising:
an electrically non-conductive layer;
a radiator formed on a first side of the electrically non-conductive layer, the radiator being configured to be coupled to the substrate layer;
a feed, the feed being electrically connected to the radiator; and
a ground layer formed on a second side of the electrically non-conductive layer to be electrically isolated from the radiator, the first side of the electrically non-conductive layer being opposite the second side of the electrically non-conductive layer;

a garment configured to hold the plurality of antennas in a predetermined arrangement for coupling to the substrate layer, the garment comprising:
  a dielectric layer having a first side configured to engage the ground layer of each antenna in the plurality of antennas; and
  an electrically conductive layer positioned on a second side of the dielectric layer, the first side of the dielectric layer being opposite the second side of the dielectric layer;
a substrate measurement device, the substrate measurement device configured to identify the at least one predetermined electrical property of the substrate layer; and
a selector, the selector having a processor configured to execute a computer program to select one antenna in the plurality of antennas with reference to at least one of the input impedance, resonant frequency, and predetermined radiation pattern of the one antenna for coupling with the substrate layer with reference to the identified one predetermined property of the substrate layer.

2. The antenna system of claim 1, at least one antenna in the plurality of antennas further comprising:
  a first slot formed through the radiator; and
  a second slot formed through the ground layer.

3. The antenna system of claim 1, at least one antenna in the plurality of antennas further comprising:
  a top conductive layer configured to contact the substrate layer, the top conductive layer being electrically connected to the ground layer; and
  a dielectric layer positioned between the top conductive layer and the radiator.

4. The antenna system of claim 1, at least one antenna in the plurality of antennas further comprising:
  a signal enhancing material applied to the radiator and configured to couple to the substrate layer.

5. The antenna system of claim 1, at least one antenna in the plurality of antennas being configured to radiate microwave radio energy through the tissue covered by the substrate layer.

* * * * *